United States Patent [19]
Toriuchi et al.

[11] Patent Number: 4,582,775
[45] Date of Patent: Apr. 15, 1986

[54] DIFFUSION TRANSFER COLOR PHOTOGRAPHIC MATERIAL WITH MESO-IONIC 1,2,4-TRIAZOLIUM-3-THIOLATE ANTIFOGGANT

[75] Inventors: Masaharu Toriuchi; Morio Yagihara; Koki Nakamura, all of Kanagawa, Japan

[73] Assignee: Fuji Photo Film Co., Ltd., Kanagawa, Japan

[21] Appl. No.: 689,692

[22] Filed: Jan. 8, 1985

[30] Foreign Application Priority Data

Jan. 9, 1984 [JP] Japan ................................ 59-1668

[51] Int. Cl.[4] .................... G03C 1/40; G03C 5/54; G03C 1/34
[52] U.S. Cl. ............................. 430/219; 430/240; 430/445; 430/489; 430/611
[58] Field of Search ............... 430/219, 240, 445, 489, 430/611

[56] References Cited

U.S. PATENT DOCUMENTS 4,139,379  2/1979  Chasman et al. ............... 430/223
4,351,896  9/1982  Altland et al. .................. 430/611
4,404,390  9/1983  Altland et al. .................. 430/611
4,459,351  7/1984  Adin et al. ..................... 430/223

Primary Examiner—Richard L. Schilling
Attorney, Agent, or Firm—Sughrue, Mion, Zinn, Macpeak, and Seas

[57] ABSTRACT

A color diffusion transfer photographic light-sensitive material comprising a support, at least one silver halide layer on the support, said emulsion layer being associated with a dye-providing compound, and an image-receiving layer on the same support as above or on another support, wherein said photographic light-sensitive material is able to provide a transferred dye image composed of a diffusible dye or its precursor released or derived from the dye-providing compound as a result of development under a strong alkaline condition in the presence of at least one meso ionic 1,2,4-triazolium-3-thiolate compound. In the present material, fog can be prevented efficiently without causing the problems of a reduction in sensitivity and a decrease in rate of development.

10 Claims, No Drawings

DIFFUSION TRANSFER COLOR PHOTOGRAPHIC MATERIAL WITH MESO-IONIC 1,2,4-TRIAZOLIUM-3-THIOLATE ANTIFOGGANT

FIELD OF THE INVENTION

The present invention relates to instant photography, and more particularly to a novel diffusion transfer color photographic light-sensitive material for use in such instant photography.

BACKGROUND OF THE INVENTION

Instant photography is well known in which transfer dye images are instantly formed utilizing the color diffusion transfer process. In this instant photography, there is generally used a photographic film unit including at least one silver halide emulsion layer on a support, said emulsion layer containing dye-providing compounds, and an image-receiving layer to fix therein diffusible dyes as color images, which is provided on the same support as above or a different support, and an alkaline aqueous processing solution is extended between the two sheet-like photographic elements (i.e., a light-sensitive element and an image-receiving element, or a light-sensitive element and a cover sheet) to thereby form dye images. In addition, a tank development type material comprising a single sheet as described in Japanese Patent Application (OPI) No. 119345/82 (the term "OPI" as used herein means a "published unexamined Japanese patent application") is of course known.

The most important of requirements for these diffusion transfer photographic light-sensitive materials, as can be readily understood from the term "instnat photography", is that the desired image can be formed in very short periods of time. When, for example, the formation of images is intended to be completed within 1 minute, it is necessary for the development of silver to be completed in as short a time as possible, i.e., within the time of from 10 to 15 seconds, because a considerably long time is needed for the diffusion (or release) of image-forming substances following the silver development.

It is well known that high-speed development increases fog, resulting in a deterioration in discrimination (Ag°max/Ag°min ratio). Moreover, as is well known, the diffusion transfer process suffers from a serious disadvantage that fog is markedly increased since it uses a 1N or more alkaline processing solution. Such an abnormally high degree of fog is a characteristic problem of the diffusion transfer process in that the development must necessarily be achieved at high speeds incomparable with those for the conventional light-sensitive materials, and also the development must necessarily be performed under high alkalinity conditions which are not involved in the conventional light-sensitive materials. The term "fog" as used herein means a so-called fog ascribable to silver halide but not a "stain".

Such an increase in fog exerts the following adverse influences: when dye-providing compounds forming an imagewise image relative to a silver image (hereinafter referred to as "negative dye-providing compounds") are used, Dmin is high and the white ground is contaminated, whereas when dye-providing compounds forming a reverse imagewise image relative to a silver image (hereinafter referred to as "positive dye-providing compounds") are used, Dmax drops. The case is the same with the silver salt diffusion transfer process.

It has thus been strongly desired to prevent the formation of fog in the diffusion transfer process.

Various techniques have been proposed for the prevention of fog, including a method using such compounds as 1-phenyl-5-mercaptotetrazole as described in U.S. Pat. No. 3,265,498, a method using blocked development inhibitors as described in U.S. Pat. Nos. 3,698,898, 4,009,029, West German Patent Application (OLS) No. 2,427,183, U.S. Pat. No. 3,265,498, etc., and a method using mercapto compounds as described in U.S. Pat. Nos. 4,355,092 and 4,355,101. These methods, however, fail to attain the object satisfactorily. That is, although they permit the prevention of fog, an undesirable problem arises in that the rate of development is seriously reduced, while on the other hand when the rate of development is less seriously reduced, the effect of fog prevention is small. This is prominent especially for cases in which a silver halide emulsion is a negative meulsion forming a surface late image. The reason for this is believed to be that the negative emulsion is especially readily fogged because of its surface sensitivity and, furthermore, the rate of development of fog is high.

Moreover, the conventional fog-preventing compounds undesirably decrease sensitivity.

SUMMARY OF THE INVENTION

An object of the present invention is to provide a color diffusion transfer photographic light-sensitive material in which Dmax is high, Dmin is low, and the rate of dye diffusion to form a color image is high.

Another object of the present invention is to provide a color diffusion transfer process which permits effectively preventing the formation of fog without causing the problems of a decrease in sensitivity and a reduction in the rate of development.

It has been found that the objects are attained by developing in the presence of meso-ionic 1,2,4-triazolium-3-thiolate compounds.

The present invention relates to a color diffusion transfer photographic light-sensitive material comprising a light-sensitive element, i.e., at least one silver halide emulsion layer provided on a support, said emulsion layer containing a dye-providing compound, and an image-receiving element, i.e., an image-receiving layer provided on the same support or different support, which fixes therein a diffusible dye or its precursor released or derived from the above dye-providing compound as a result of development under strong alkaline conditions, which is characterized in that it is developed in the presence of at least one meso-ionic 1,2,4-triazolium-3-thiolate compound.

DETAILED DESCRIPTION OF THE INVENTION

In the light-sensitive material of the present invention, it has been confirmed that when negative dye-providing compounds are used, Dmin drops without a reduction in Dmax and sensitivity and also a decrease in the rate of development occurs, and when positive dye-providing compounds are used, Dmax is increased efficiently without causing the problems of a reduction in contrast due to a delay in development and a decrease in sensitivity. This effect could not be expected at all from European Patent No. 0054415A1. That is, it is described in this European patent that the meso-ionic 1,2,4- triazolium-3-thiolate compounds of the present invention are used for photographic purposes. These compounds, however, are used only as stabilizing or fixing agents for silver halide to be used in so-called heat developable photography in which heat treatment is applied to achieve development and fixation. Since such stabilizing or fixing agents for silver halide form water-soluble and light-insensitive Ag (I) complexes through exposure and processing of light-sensitive material, their effect is essentially different from the effect of the present invention, i.e., prevention of fog in the color diffusion transfer process in which wet processing is carried out even under strong alkaline conditions.

The meso-ionic 1,2,4-triazolium-3-thiolate compounds of the present invention are preferably those compounds represented by the following general formula (I)

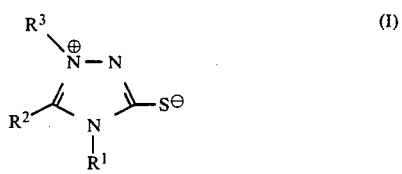

wherein,
$R^1$ is a hydroxyl group, a substituted or unsubstituted alkyl group, a substituted or unsubstituted alkenyl group, a substituted or unsubstituted aryl group, a substituted or unsubstituted heterocyclic group, $-NR^4R^5$ wherein $R^4$ and $R^5$ are each a hydrogen atom, a substituted or unsubstituted alkyl group, a substituted or unsubstituted acyl group, a substituted or unsubstituted aryl group or $R^4$ and $R^5$ may combine together to form a nitrogen-containing hetero ring, a substituted or unsubstituted acyloxy group, or a substituted or unsubstituted alkoxyl group;
$R^2$ is a hydrogen atom, a substituted or unsubstituted alkyl group, a substituted or unsubstituted aryl group, or a substituted or unsubstituted heterocyclic group; and
$R^3$ is a substituted or unsubstituted alkyl group, a substituted or unsubstituted alkenyl group, a substituted or unsubstituted aryl group, or a substituted or unsubstituted heterocyclic group; and
$R^1$ and $R^2$ or $R^2$ and $R^3$ may combine together to form a 5- to 7-membered, saturated or unsaturated, carbon ring or hetero ring.

The groups represented by $R^1$ to $R^5$ will hereinafter be explained in detail.

The substituted or unsubstituted alkyl group may be straight or branched, or cyclic. When it is straight or branched, the number of carbon atoms (including those of a substitutent or substituents when the alkyl group is substituted; this is applicable to the aryl group and other groups) is generally from 1 to about 30 and preferably 10 or less. In the case of cyclic alkyl and alkenyl groups, it is generally from 3 to about 30 and preferably not more than 10. The number of carbon atoms in each of the aryl group and the heterocyclic group is generally from 1 to about 30 and preferably not more than 10.

Suitable examples of substituents for the alkyl, alkoxyl and alkenyl groups are an alkoxyl group, an alkoxycarbonyl group, an amino group (including an amino group substituted by one or two alkyl groups, and a cyclic amino group), an alkylthio group, a carbonamido group, a carbamoyl group, a carboxyl group, a sulfo group, a hydroxyl group, an aryl group (including a phenyl group, a naphthyl group, and their substituted derivatives), a heterocyclic radical (preferably a 5 or 6-membered ring, e.g., tetrazol-5-yl and triazolin-3-one-4-yl), a fluorine atom, a sulfamoyl group, a sulfonamido group, $-SO-R^6$ (wherein $R^6$ is a substituted or unsubstituted alkyl or aryl group), $-SO_2-R^7$ (wherein $R^7$ is the same as $R^6$), etc.

Suitable examples of substituents for the aryl, heterocyclic, acyl and acyloxy groups include, as well as the substituents given above for the alkyl group and so forth, a nitro group, a halogen atom, an alkyl group, an aryl group, and a cyano group.

The above hetero ring is preferably a 5- or 6-membered ring containing nitrogen, oxygen or sulfur as the hetero atom.

Preferred among the groups represented by $R^1$ and $R^3$ are an unsubstituted alkyl group, a substituted alkyl group (in which the substituent is an alkoxy group, an alkoxycarbonyl group, a carbonamido group, a carbamoyl group, a sulfonamido group, or a sulfamoyl group), an unsubstituted aryl group (e.g., a phenyl group), and a substituted aryl group (in which the substituent is, for example, an alkoxycarbonyl group, a sulfamoyl group, a sulfonamido group, a carbonamido group, a carbamoyl group, a halogen atom, or a phenyl group substituted by a cyano group, for example).

Representative examples of the groups represented by $R^1$ to $R^5$ are shown below although the present invention is not limited thereto.

Representative Examples of $R^1$:
a hydroxyl group, a methyl group, a lauryl group, a 2-methoxyethyl group, an ethoxycarbonyl group, an allyl group, a 2-buten-1-yl group, a cyclopentyl group, a cyclohexyl group, a phenyl group, a 4-methoxyphenyl group, a 3,4-di-chlorophenyl group, a 4-sulfamoylphenyl group, a 4-lauroyl-amidophenyl group, a 2-pyridyl group, a 1-octylpiperidin-4-yl group, an acetoxy group, a benzoyloxy group, a methoxy group, a 2-methoxyethoxy group, etc.

Of these groups, a methyl group, a 2-methoxyethyl group, a cyclopentyl group, a cyclohexyl group, a phenyl group, a 4-methoxyphenyl group, a 3,4-dichlorophenyl group, a 4-sulfamoylphenyl group, and a 4-lauroylamidophenyl group are preferred.

Representative Examples of $R^2$:
a hydrogen atom, a methyl group, an isobutyl group, a tert-butyl group, a methylthiomethyl group, a cyclopentyl group, a cyclohexyl group, a phenyl group, a 4-methoxyphenyl group, a 4-chlorophenyl group, a 2-pyridyl group, a 2-furyl group, etc.

Of these groups, a hydrogen atom, a methyl group, an isobutyl group, a tert-butyl group, a methylthiomethyl group, a cyclopentyl group, a cyclohexyl group, a phenyl group, a 4-methoxyphenyl group, and a 4-chlorophenyl group are preferred.

Representative Examples of $R^3$:
a methyl group, an ethyl group, an octyl group, an octadecyl group, a methoxyethyl group, an allyl group, a 2-buten-1-yl group, a cyclopentyl group, a cyclohexyl group, a phenyl group, a 4-ethoxycarbonylphenyl group, a 3-sulfamoylphenyl group, a 4-methoxyphenyl group, a 4-pyridyl group, a 2-pyridyl group, etc.

Of these groups, a methyl group, an ethyl group, an octyl group, an octadecyl group, a methoxyethyl group, a cyclopentyl group, a cyclohexyl group, a phenyl group, a 4-ethoxy-carbonyl phenyl group, a 3-sulfamoyl phenyl group and a 4-methoxyphenyl group are preferred.

Representative Exampels of $R^4$ and $R^5$:

a hydrogen atom, a methyl group, an ethyl group, an ethoxycarbonylmethyl group, a 2-methoxyethyl group, an acetyl group, an octanoyl group, a phenyl group, a 4-chlorophenyl group, etc.

Preferred compounds include those in which at least one of $R^1$, $R^2$ and $R^3$ is a phenyl group or a substituted phenyl group and the sum of the carbon numbers of $R^1$, $R^2$ and $R^3$ is not less than 7.

Representative examples of the meso-ionic 1,2,4-triazolium-3-thiolate compounds of the present invention are shown below although the present invention is not limited thereto.

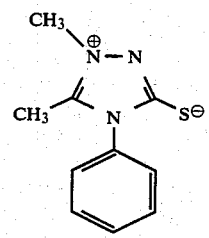

1.

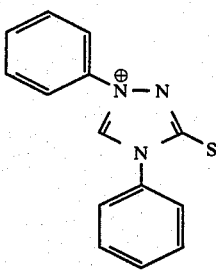

2.

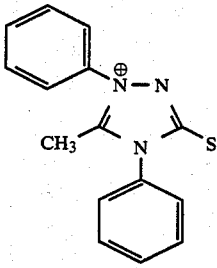

3.

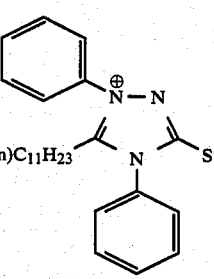

4.

-continued

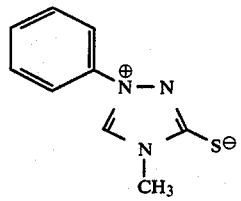

5.

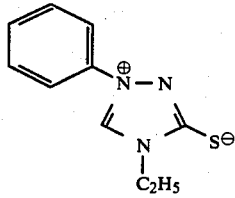

6.

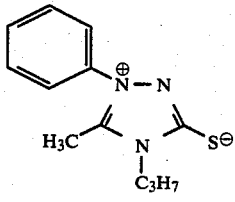

7.

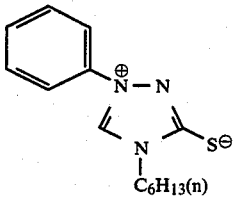

8.

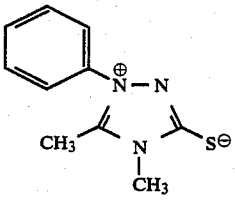

9.

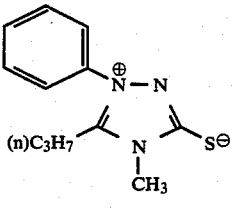

10.

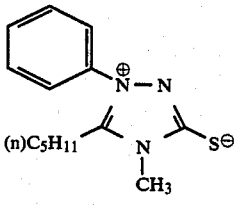

11.

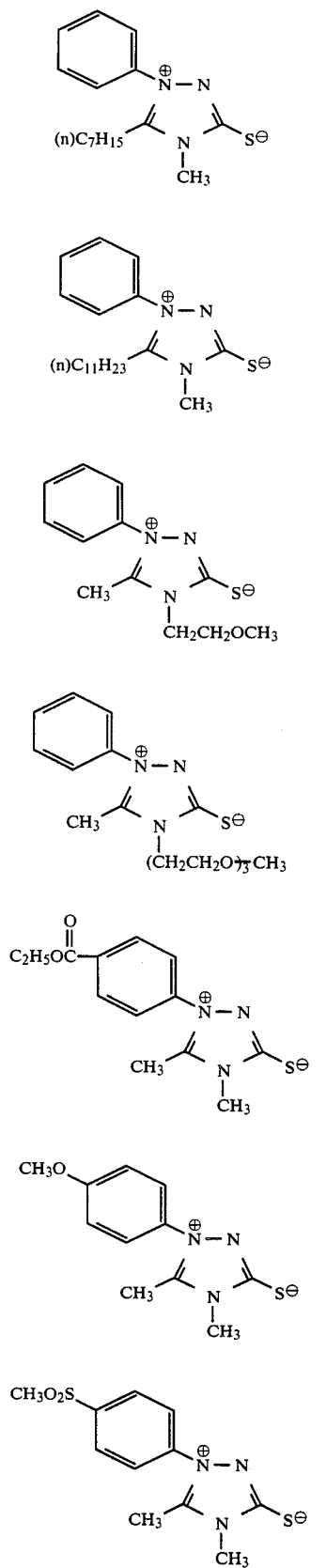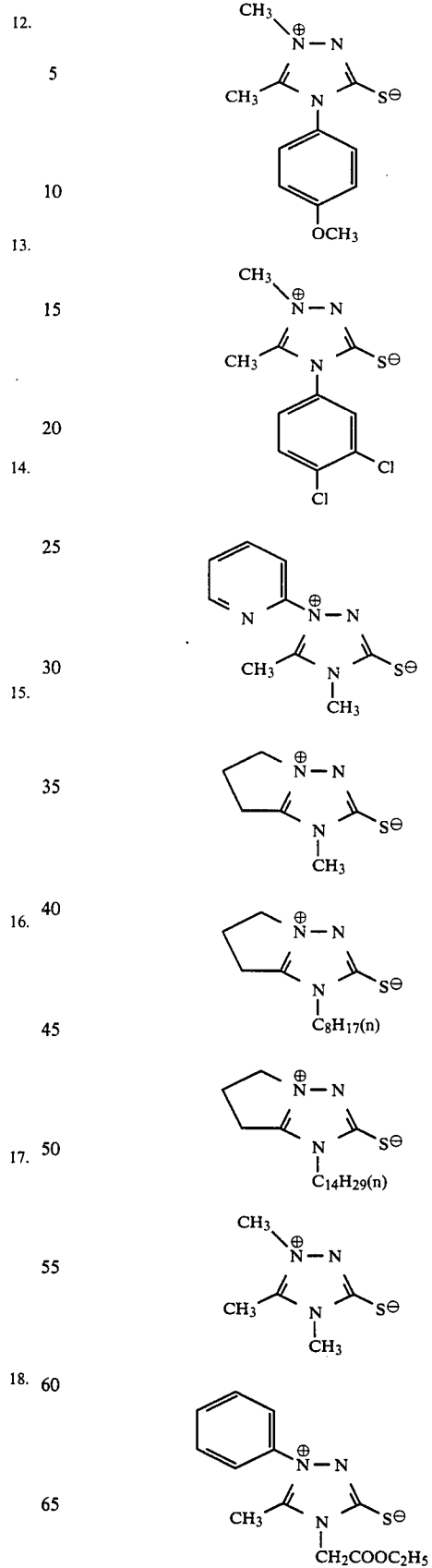

-continued

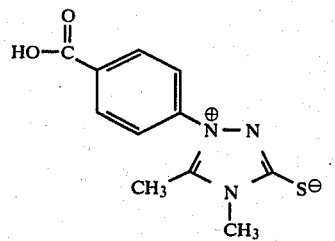

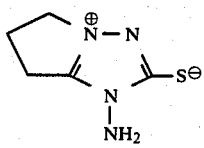

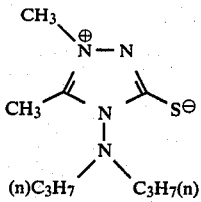

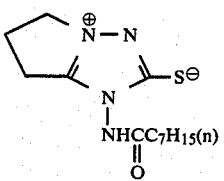

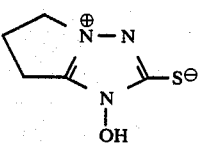

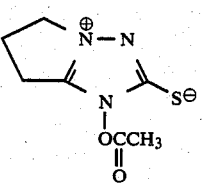

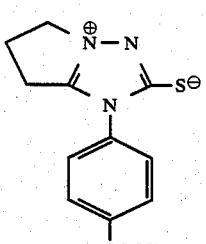

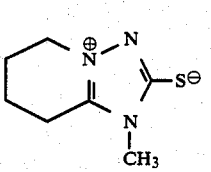

27.

28.

29.

30.

31.

32.

33.

34.

-continued

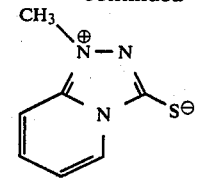 35.

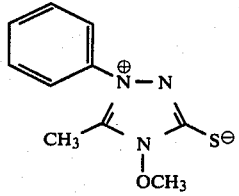 36.

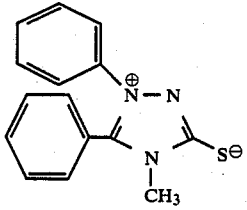 37.

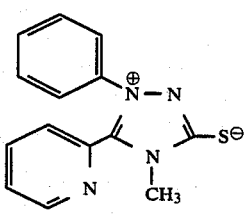 38.

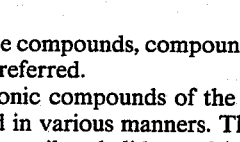

Of the above compounds, compounds 1,5,9 and 16 are particularly preferred.

The meso-ionic compounds of the present invention can be applied in various manners. That is, they can be incorporated in a silver halide emulsion layer, or a layer to be superposed on the silver halide emulsion layer (e.g., a coloring matter-containing layer, an intermediate layer, and a protective layer), or a processing solution, or a cover sheet, for example. It is especially preferred that the meso-ionic compounds of the present invention be added to a silver halide emulsion layer.

The amount of the meso-ionic compounds of the present invention being added is not critical; it is preferably from about 0.001 to 5 mol%, more preferably from 0.01 to 2 mol% per mol of silver in each silver halide emulsion layer.

When the meso-ionic compounds of the present invention are incorporated in a layer other than the silver halide emulsion layer, or in a processing solution, they are added in such amounts that are equivalent with the above-specified amounts.

In incorporating the meso-ionic compounds of the present invention in a silver halide emulsion layer, various known procedures can be employed. In addition, a procedure in which the meso-ionic compounds of the present invention are dissolved in water or alcohols and then gradually added to an emulsion-coating solution, and a procedure in which certain meso-ionic compounds are emulsified by the use of auxiliary solvents and gelatin and then added in the form of emulsions can be employed. The former procedure is generally convenient.

In the light-sensitive material of the present invention, the formation of fogged silver can be prevented efficiently without exerting adverse influences on the rate of development and sensitivity of the silver halide. Accordingly, various development-accelerating techniques can be employed in the present invention. This is one of the major advantages of the present invention. As is well known, these development-accelerating techniques generally tend to increase fogged silver and thus have been difficult to employ. In the present invention, on the other hand, the formation of fogged silver can be prevented efficiently and, therefore, even if a development-accelerating procedure is applied, the formation of fogged silver can be greatly inhibited. Thus the present invention permits the production of a diffusion transfer light-sensitive material in which images are completed at very high speeds.

In the light-sensitive material of the present invention, known development accelerators can be used in combination. Representative examples of such development accelerators are alcohols exemplified by benzyl alcohol, aminoalcohols such as aminopentanol, quaternary ammonium salts, thio ethers, and hydroquinones.

The meso-ionic compounds of the present invention can be prepared by, for example, (I) anhydro-acylation of 1,4-disubstituted thiosemicarbazides, (II) heating of 4-acyl-1,4-disubstituted thiosemicarbazides, (III) a reaction between N-aminoamidine and thiophosegen, (IV) a reaction between N-aminoamidine or N-thioacylhydrazine and isothio-cyanic acid, (V) a reaction between N-aminoamidine or N-thioacylhydrazine and carbon disulfide/dicyclohexylcarbo-diimide, and (VI) a reaction of meso-ionic, 1,3,4-thiadiazole or the corresponding methiodido with primary amines. More specifically, the meso-ionic compounds of the present invention can be synthesized by the methods described in the references as described below, or the references referred to therein.

W. Baker and W. D. Ollis, Chem. Ind. (London), 910 (1955); M. Ohta and H. Kato, in "Nonbenzenoid Aromatics"

(J. P. Snyder, ed.): K. T. Potts, S. K. Roy and D. P. Jones, J. Heterocycl. Chem. 2, 105 (1965); K. T. Potts, S. K. Roy, and D. P. Jones, J. Org. Chem. 32, 2245 (1967): G. F. Duffin, J. D. Kendall, and H. R. J. Waddington, J. Chem. Soc., 3799 (1959): R. L. Hinmann and D. Fulton, J. Amer. Chem. Soc., 80, 1895 (1958): W. D. Ollis and C. A. Ramsden, Chem. Commun., 1222 (1971): W. D. Ollis and C. A. Ramsden, J. Chem. Soc., Perkin Trans. I, 633 (1974): R. Grayshey, M. Baumann, and R. Hamprecht, Tetrahedron Lett., 2939 (1972):

Several synthesis examples are shown below.

SYNTHESIS EXAMPLE 1

Synthesis of Compound 1

On reacting 27 g of phenyl isothiocyanate and 15 g of acetylhydrazine in ethanol at room temperature, 1-acetyl-4-phenylthiosemicarbazide was formed. This 1-acetyl-4-phenylthiosemicarbazide was filtered off and heated under reflux in ethanol in the presence of sodium ethylate whereupon 3-mercapto-5-methyl-4-phenyl-1,2,4-triazole was formed.

3-Mercapto-5-methyl-4-phenyl-1,2,4-triazole (19.1 g) was suspended in 200 ml of methanol, and 20 g of 28% sodium methylate was added thereto. After 10 minutes, 15 g of methyl iodide was added dropwise. They were reacted for 2 hours and then the methanol was distilled away. Upon extraction of the residue with ethyl acetate, 5-methyl-3-methylthio-4-phenyl-1,2,4-triazole was obtained.

The thus-prepared 5-methyl-3-methylthio-4-phenyl-1,2,4-triazole (10 g) was mixed with 40 g of methyl iodide and heated under reflux for 4 hours.

Crystals precipitated were filtered off and recrystallized from ethanol. This compound was 1,5-dimethyl-3-methylthio-4-phenyl-1,2,4-triazolium iodide, m.p., 212°–214° C. (yield: 70%).

The above compound (10 g) was suspended in 50 ml of pyridine and heated under reflux for 30 hours. The pyridine was distilled away under reduced pressure, and upon addition of ethanol, crystals precipitated. This compound was identified as Compound 1 by NMR, IR, and Mass spectral analyses. The amount of the compound, m.p., 229°–230° C. was 2.1 g (yield: 35.6%).

SYNTHESIS EXAMPLE 2

Synthesis of Compound 4

1,4-Diphenylthiosemicarbazide (12.2 g) was added to 100 ml of toluene and then stirred. Subsequently, 13.0 g of lauroyl chloride was added at room temperature. They were reacted at room temperature for 30 minutes and, thereafter, the reaction mixture was heated and refluxed for 8 hours. It was cooled and then the toluene was distilled away under reduced pressure. The residue was dissolved in ethanol. Upon addition of ammonia water, colorless crystals were formed. These crystals were filtered off and recrystallized from a chloroform-/hexane mixture. The amount of the compound, m.p., 205°–208° C. was 8.7 g (yield: 42.6%).

SYNTHESIS EXAMPLE 3

Synthesis of Compound 5

Methyl isothiocyanate (73 g) was dissolved in 500 ml of benzene and then stirred. Subsequently, 108 g of phenylhydrazine was added at room temperature. The mixture was heated and refluxed for 5 hours. Upon cooling, 4-methyl-1-phenylthiosemicarbazide precipitated, which was then filtered off. The amount of the compound was 122 g (yield: 67.4%).

The thus-prepared 4-methyl-1-phenylthiosemicarbazide can be used in the subsequent reaction without further purification.

4-Methyl-1-phenylthiosemicarbazide (18.1 g) was added to 150 ml of formic acid and then heated under reflux for 20 hours. The reaction mixture was cooled and then crystals precipitated were filtered off and recrystallized from methanol whereupon meso-ionic 4-methyl-1-phenyl-1,2,4-triazolium-3-thiolate was obtained as light yellow crystals. The amount of the compound, m.p., 247°–249° C. was 3.8 g (yield: 20.0%).

SYNTHESIS EXAMPLE 4

Synthesis of Compound 9

4-Methyl-1-phenylthiosemicarbazide (18.1 g) as prepared in Synthesis Example 1 and 25 ml of acetic acid were mixed at room temperature, and 25 ml of acetic anhydride was added, stirred and heated under reflux for 8 hours. As the reaction proceeded, crystals precipitated. After the reaction mixture was cooled, the crystals were filtered off and recrystallized from a methanol/acetic acid mixture wehreupon colorless crystals of Compound 7 were obtained. The amount of the compound, m.p., 290°–292° C., was 13.2 g (yield: 64.4%).

SYNTHESIS EXAMPLE 5

Synthesis of Compound 14

1-Phenyl-4-methylthiosemicarbazide (10 g) as prepared in Synthesis Example 3 was mixed with toluene, and then 9 g of hexanoyl chloride was added and stirred at room temperature. The mixture was then heated and refluxed for 5 hours.

The toluene was distilled away under reduced pressure, and the residue was dissolved in ethanol. Upon addition of small portions of ammonia water, crystals of Compound 9 precipitated. The compound was recrystallized from isopropyl alcohol. The amount of the compound, m.p., 137°–139° C., was 4.0 g (yield: 27.8%).

SYNTHESIS EXAMPLE 6

Synthesis of Compound 12

2-Methoxyethyl isothiocyanate (11.7 g) was dissolved in benzene and stirred, and 11.9 g of phenyl hydrazine was added at room temperature and then heated under reflux. They were reacted for 6 hours and then cooled, and crystals precipitated were filtered off. The yield was 66.7%.

The thus-prepared 4-(2-methoxyethyl)-1-phenylthiosemicarbazide can be used in the subsequent reaction without further purification.

4-(2-Methoxyethyl)-1-phenylthiosemicarbazide (10.0 g) was dissolved in 15 ml of acetic acid with stirring. Then 15 ml of acetic anhydride was added and heated under reflux for 8 hours. After the reaction was completed, the reaction mixture was cooled and the solvent was distilled away. The reaction product was purified by chromatography using silica gel and then recrystallized from an isopropyl alcohol-diethyl ether. The amount of the compound, m.p., 108°–109° C., was 2.1 g (yield: 19.0%).

SYNTHESIS EXAMPLE 7

Synthesis of Compound 16

A mixture of 9.3 g of 4-ethoxycarbonylphenyl hydrazine and 3.6 g of methyl isothiocyanate was dissolved in 100 ml of benzene. The resulting solution was heated under reflux with stirring. After 5 hours, the reaction mixture was cooled and crystals precipitated were filtered off, whereupon 1-(4-ethoxycarbonylphenyl)-4-methylthiosemicarbazide was obtained in the form of colorless crystals.

The thus-prepared 1-(4-ethoxycarbonylphenyl)-4-methyl-thiosemicarbazide can be used in the subsequent reaction without further purification.

1-(4-Ethoxycarbonylphenyl)-4-methylthiosemicarbazide (6.5 g) was added to 10 ml of acetic acid, and then 10 ml of acetic anhydride was added. The mixture was heated under reflux. After the reaction was completed, the reaction mixture was cooled, and crystals precipitated were recrystallized from methanol. The amount of the compound, m.p., 248°–250° C., was 1.8 g (yield: 25.4%).

SYNTHESIS EXAMPLE 8

Synthesis of Compound 22

γ-Bromobutyric acid and 5 times the molar quantity of hydrazine hydrate were dissolved in methanol and heated under reflux for 7 hours. The methanol was distilled away under reduced pressure and then the residue was passed through a column packed with alumina. Fractions eluted by this column chromatography were collected. In this case, a methanol/chloroform (20:1) mixture was used as an eluent. Upon distillation of the solvent of the eluted fractions, 1-amino-2-pyrrolidinone was obtained.

1-Amino-2-pyrrolidinone (10 g) was dissolved in toluene, and 7.3 of methyl isothiocyanate was added. The resulting mixture was heated under reflux for 3 hours. After the reaction mixture was cooled, crystals precipitated were collected by filtration and then dried. This compound was identified as 1-(2-pyrrolidinone-1-yl)-3-methylthiourea by NMR and Mass spectral analyses.

1-(2-Pyrrolidinone-1-yl)-3-methylthiourea (14 g) was added to 20 ml of acetic acid and then stirred. Subsequently 20 ml of acetic anhydride was added, and the resulting mixture was heated under reflux. After the reaction was completed, the solvent was distilled away, and the reaction product was recrystallized from ethanol. The amount of the compound, m.p., 257°–259° C., was 3.4 g (yield: 27.1 g).

Silver halide emulsions as used herein are hydrophilic colloidal dispersions of silver chloride, silver bromide, silver chlorobromide, silver iodobromide, silver chloroiodobromide, or mixtures thereof. The halogen composition of silver halide can vary over a wide range. Particularly preferred are silver bromide, silver iodobromide, and silver chloroiodobromide each having an iodide content of not more than 10 mol% and a chloride content of not more than 30 mol%. These silver halide emulsions can be, if desired, treated with spectral sensitizing dyes to impart extended color sensitivity. Spectral sensitizing dyes which can be used for this purpose include cyanine dye and merocyanine dye.

In the light-sensitive material of the present invention, an internal latent image-type silver halide emulsion can also be used. Examples of emulsions of this type are a conversion type emulsion, a core/shell type emulsion, and an emulsion in which different metals are incorporated as described in, for example, U.S. Pat. Nos. 2,592,250, 3,206,313, 3,447,927, 3,761,276, and 3,935,014.

Of the above silver halide emulsions, a high sensitivity negative emulsion forming a surface latent image is particularly useful. Any high sensitivity negative emulsions that have been known can be used. As one of these negative emulsions, an emulsion containing tablet silver halide grains as described in, for example, Research Disclosure, No. 22534 (1983), and West German Patent Application (OLS) No. 3,241,642 is also suitable for use.

It is believed that the effect of the present invention is especially greatly exhibited for such surface latent image-type emulsions since they increase fogged silver, as described above, when used in the diffusion transfer proess. It has been determined that when the surface latent image-type emulsions are used, a difference in the rate of development between exposed areas (where the amount of precipitated silver is the largest) and unexposed areas (wherein the amount of precipitated silver is the smallest) is small. Based on the above findings, it has been found that the meso-ionic 1,2,4-triazolium-3-thiolate compounds of the present invention are more effective when incorporated in a silver halide emulsion layer or a layer in the neighbourhood of the silver halide emulsion layer. It is particularly preferred that they be incorporated in a red-sensitive emulsion layer (in particular, an emulsion provided with red-sensitivity by trimethine-based cyanine sensitizing dyes) or in the neighbourhood thereof.

Immobile dye-providing compounds releasing a diffusible dye (including its precursor) as the result of development under alkaline conditions (dye-providing compound) may be negative working color-providing compounds or positive working color-providing compounds. The latter are preferred for the purpose of producing positive transfer dye images.

Typical examples of such negative working dye providing compounds are N-substituted sulfonamide type redox compounds releasing a dye through oxidation followed by hydrolysis.

Typical examples of positive working dye-providing compounds which can be used in the present invention are compounds having a positive working redox nucleus, as described in, for example, U.S. Pat. Nos. 4,139,379, 4,139,389, 4,199,354, 4,199,355, 4,371,604, Japanese Patent Application (OPI) Nos. 111628/74, 63618/76, 4819/77. 69033/78, 130927/79, 119345/82, and 185333/84.

Positive working dye-providing compounds which are suitable for use in the present invention are immobile dye-providing compounds releasing a diffusible dye on receiving at least one electron. These compounds are often used in combination with non-diffusible electron donating compounds (hereinafter referred to merely as "ED compounds"). These ED compounds are strong reducing compounds or their precursors present in an emulsion layer or its adjacent layer. Representative examples of such compounds are described in U.S. Pat. Nos. 4,278,750, 4,263,393, and Japanese Patent Application (OPI) No. 138736/81. Incorporation of such ED compounds in an emulsion layer or in the neighbourhood thereof increases fogged silver in the silver halide emulsion. In the light-sensitive material of the present invention, the formation of fogged silver due to the addition of ED compounds can be prevented efficiently. That is, the present invention is very effective in preventing fogged silver due to the addition of ED compounds. As a matter of course, dye-providing compounds in which a dye-providing compound and an ED compound are combined together into one body, i.e., dye-providing compounds also having the function of the ED compound increase fogged silver.

Of these dye-providing compounds, compounds having the structure as shown below are particularly preferred, although the present invention is not limited thereto. In addition, compounds of the type wherein a positive working redox nuclues and an ED compound are contained in the molecule are suitable to use in the present invention.

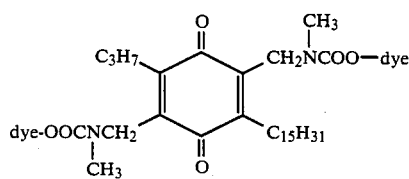

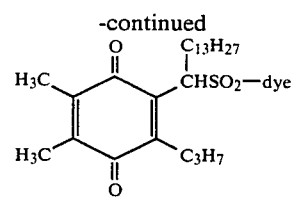

In addition, as positive working dye-providing compounds, dye developing agents that diffuse under alkaline conditions can be used.

Dyes prepared from dye-providing compounds that are used in the present invention may be those dyes which have been prepared in advance, or dye precursors capable of being converted into the corresponding dyes during the process of photographic processing or additional processing. The ultimate image dye may or may not be in the form of metal complexes. Typical dyes which are useful for use in the present invention are azo dyes, azomethine dyes, anthraquinone dyes, and phthalocyanine dyes which have been converted or not converted into a metal complex form. Of these dyes, azo-based cyan, magenta, and yellow dyes are particularly important.

Examples of the dye portions which can be used in the present invention are shown below along with representative examples of negative working dye-providing compounds. These dye portions, if only the connecting portion is changed, can be used as positive working dye-providing compounds which are combined together with positive working redox nuclei.

Representative examples of yellow dye-providing compound are described in Japanese Patent Publication No. 2618/74, U.S. Pat. No. 3,309,199, Japanese Patent Publication No. 12140/82, Japanese Patent Application (OPI) Nos. 114930/76, 111344/79, 16130/81, 71072/81, 79031/79, 64036/78, 23527/79, U.S. Pat. Nos. 4,148,641, 4,148,643, Research Disclosure, No. 17630 (1978) and No. 16475 (1977).

Representative examples of magenta dye-providing compounds are described in U.S. Pat. No. 3,453,107, Japanese Patent Publication No. 43950/71, Japanese Patent Application (OPI) No. 106727/77, U.S. Pat. Nos. 3,932,380, 3,931,144, 3,932,308, Japanese Patent Application (OPI) Nos. 115528/75, 106727/77, 23628/78, 65034/79, 36804/80, 161332/79, 4028/80, 73057/81, 71060/81, 134/80, 35533/78, U.S. Pat. Nos. 4,207,104, 4,287,292, 4,357,410, and 4,357,412.

Representative examples of cyan dye-providing compounds are described in Japanese Patent Publication No. 32130/73, Japanese Patent Application (OPI) Nos. 8827/77, 126331/74, 109928/76, 99431/79, 149328/78, 8827/77, 47823/78, 143323/78, 99431/79, 71061/81, 64035/78, 121125/79, U.S. Pat. Nos. 4,142,891, 4,195,994, 4,147,544, 4,148,642, European Pat. Nos. 53,037, 53,040, Research Disclosure, No. 17630 (1978) and No. 16475 (1977).

As one kind of dye precursors, dye-releasing redox compounds having a dye portion whose light absorption is temporarily shifted in a light-sensitive element can be used in the present invention. Representative examples of such compounds are described in Japanese Patent Application (OPI) Nos. 53330/80, 53329/80, U.S. Pat. Nos. 3,336,287, 3,579,334, 3,982,946, and British Patent No. 1,467,317.

As developing agents to be used in the present invention, any silver halide developing agents can be used as long as they are capable of undergoing cross oxidation with desired compounds (e.g., dye-providing compounds and ED compounds). These developing agents may be incorporated into an alkaline processing composition, or may be added to a suitable layer of the light-sensitive material. Representative examples of developing agents which can be used in the present invention are shown below.

Hydroquinones, aminophenols, phenylenediamines, pyrazolidinones (e.g., phenidone, 1-m-tolyl-4-hydroxymethyl-4-methyl-3-pyrazolidinone, dimethone, 1-p-5olyl-4,4-dihydroxymetyl-3-pyrazolidinone, 1-p-tolyl-4-methyl-4-hydroxymethyl-3-pyrazolidinone, 1-(4'-methoxyphenyl)-4-methyl-4-hydroxymethyl-3-pyrazolidinone, and 1-phenyl-4-methyl-4-hydroxymethyl-3-pyrazolidinone), etc., as described in Japanese Patent Application (OPI) No. 16131/81.

Of the above compounds, black-and-white developing agents (in particular, pyrazolidinones) are particularly preferred, which generally reduce the formation of stain in an image-receiving layer compared with color developers such as phenylenediamines.

Suitable processing compositions for use in processing of the light-sensitive materials of the present invention contain bases such as sodium hydroxide, potassium hydroxide, sodium carbonate, and sodium phosphate, and have a pH of about 9 or more. Preferably they have a pH of at least 11.5. The processing composition may contain antioxidants such as sodium sulfite, ascorbic acid salts, and piperidinohexose reductone, and also silver ion concentration-controling agents such as potassium bromide. In addition, tackifiers such as hydroxyethyl cellulose and sodium carboxymethyl cellulose may be incorporated into the processing composition.

In addition, in the alkaline processing compositon, compounds having an action of accelerating development or of accelerating the diffusion of dyes, such as benzyl alcohol, may be incorporated.

When the light-sensitive material of the present invention constitutes at least one part of a film unit comprising a light-sensitive element, an image-receiving element (these elements may be combined together into one body), a processing element (a processing composition), and if desired, a cover sheet, it is preferred to use the processing composition in containers rupturable on application of pressure, as described in U.S. Pat. Nos. 2,543,181, 2,642,886, 2,653,732, 2,723,051, 3,056,491, 3,056,492, and 3,152,515.

In reproduction of natural colors by the subtractive color process, there is used a light-sensitive material comprising at least two combinations of an emulsion having selective spectral sensitivity in a certain wavelength region and a coloring matter having selective spectral absorption in the same wavelength region as above.

Particularly useful is a light-sensitive material comprising a combination of a blue-sensitive silver halide emulsion and a yellow dye-providing compound, a combination of a green-sensitive emulsion and a magenta dye-providing compound, and a combination of a red-sensitive emulsion and a cyan dye-providing compound. These emulsion/dye-providing compound combination units may be coated in a superposed layer form and in a face-to-face ralation, or alternatively they are formed in an individual grain form (in which the dye-providing compound and the silver halide grain are present in the same grain) and coated as a single layer.

Scavengers for oxidized developing agents can be used in various intermediate layers of the light-sensitive material of the present invention. Suitable examples are described in *Research Disclosure*, Vol. 151 (November 1976), pp. 76–79.

Between an intermediate layer and a dye-providing compound containing layer may be provided a separating layer as described in Japanese Patent Application (OPI) No. 52056/80. In an intermediate layer, silver halide emulsions may be incorporated as described in Japanese Patent Application (OPI) No. 67850/81.

To the light-sensitive material of the present invention can be applied a mordanting layer, a neutralizing layer, a neutralization rate-controlling layer (a timing layer), and so forth as described in, for example, U.S. Pat. No. 4,268,625.

In producing a color photograph, the light-sensitive material of the present invention is processed as follows.

The light-sensitive material (or a light-sensitive element) is first exposed imagewise. Then the material is processed with an alkaline processing composition in the presence of a developing agent (an electron transfer agent) and a meso-ionic 1,2,4-triazolium-3-thiolate compound to develop the exposed silver halide emulsion. As a result of the development of the silver halide emulsion, a pattern of a diffusible dye is formed corresponding to the image. Then at least a part of the dye is diffused or transferred to an image-receiving layer (or an image-receiving element). In this way, a diffusion transfer color image is formed in the image-receiving layer.

In addition, in the same manner as above, a color photograph can be produced by utilizing dyes remaining in the light-sensitive material (or the light-sensitive element).

The light-sensitive material of the present invention, in one embodiment, is, as described above, a light-sensitive element (1) comprising a support and at least one silver halide emulsion layer coated on the support. In another embodiment, the light-sensitive material of the present invention comprises the light-sensitive material (1) and an image-receiving element (or an image-receiving layer) (2). In addition, a light-sensitive material (or a film unit) comprising the light-sensitive element (1), the image-receiving element (2), and a means to supply a processing composition (3) is also included in the scope of the present invention.

In the above last embodiment, containers to supply the processing composition are disposed so that their contents, i.e., the processing composition is supplied between a light-sensitive layer and a cover sheet, or a light-sensitive layer and an image-receiving layer, for example.

The above image-receiving element may be prepared using another support so that after imagewise exposure the light-sensitive element can be superposed on the image-receiving element. This embodiment is described in U.S. Pat. No. 3,362,819, for example. As another embodiment, the image-receiving element may be always kept in contact with the light-sensitive material through the period from prior to exposure to after exposure.

In addition, as another embodiment, the image-receiving element may be formed on the same support as that on which the light-sensitive element is formed. A film unit of this type is described in Belgian Patent No. 757,960, for example. Its modified form is described in Belgian Patent No. 757,959.

As another embodiment, a peeling layer may be provided between the image-receiving layer and the light-sensitive element. In this case, after the formation of transferred images, the image-receiving layer can be separated from the light-sensitive element and used as a color print or color slide in the usual form.

The present invention is described in greater detail with reference to the following examples which are not meant to be limiting.

Unless otherwise specified, all ratios, percentages, etc. are by weight.

EXAMPLE 1

Laminate-type color diffusion transfer light-sensitive sheet Nos. 1 to 8, a cover sheet, and a processing solution were prepared as follows.

Preparation of Light-Sensitive Sheets

The following layers were provided on a polyethylene terephthalate transparent support in this order to prepare light-sensitive sheet Nos. 1 to 8.

(1) Image-receiving layer containing 3.0 g/m² of a copolymer of styrene and N-vinylbenzyl-N-methylpiperidinium chloride and 3.0 g/m² of gelatin.

(2) White reflective layer containing 20 g/m² of titanium dioxide and 2.0 g/m² of gelatin.

(3) Light-shielding layer containing 2.0 g/m² of carbon black and 1.0 g/m² of gelatin.

(4) Layer containing $1.5 \times 10^{-4}$ mol/m² of cyan dye-providing as shown below, $1.5 \times 10^{-4}$ mol/m² of an ED compound A as shown below 0.1 g/m² of N,N-diethyllaurylamide, and 0.8 g/m².

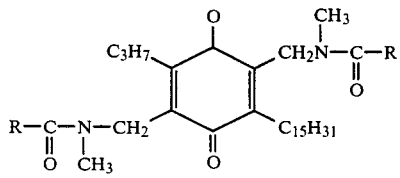

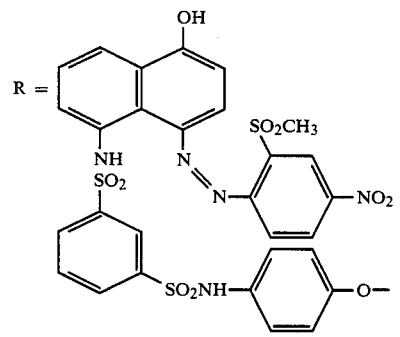

(5) Layer containing 1.0 g/m² (calculated as silver) of a red-sensitive surface latent image-type silver iodobromide emulsion, 0.02 mol/mol Ag of a compound as shown in Table 1, 0.01 g/m² of N,N-diethyllaurylamide, and 0.6 g/m² of gelatin.

(6) Layer containing 0.5 g/m² of 2,5-di-tertpentadecylhydroquinone and 0.4 g/m² of gelatin.

(7) Layer containing $2 \times 10^{-4}$ mol/m2 of a magenta dye-providing compound having the structure shown below, $2 \times 10^{-4}$ mol/m² of an ED compound as shown below, 0.1 g/m² of N,N-diethyllaurylamide, and 0.8 g/m² of gelatin.

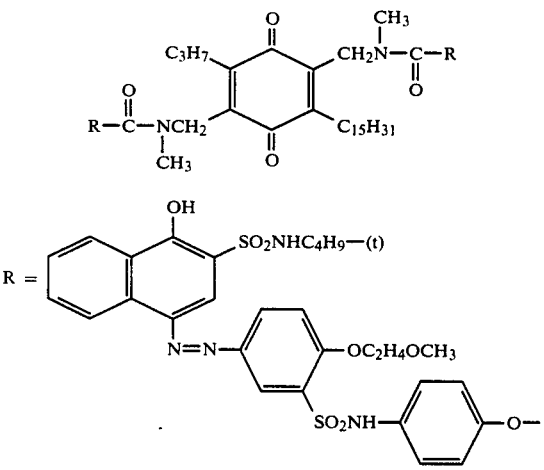

(8) Layer containing 1.0 g/m² (calculated as silver) of a green-sensitive surface latent image-type silver iodobromide emulsion, 0.01 mol/mol Ag of a compound as shown in Table 1, 0.01 g/m² of N,N-diethyllaurylamide, and 0.6 g/m² of gelatin.

(9) Same as Layer (6) above.

(10) Layer containing $3 \times 10^{-4}$ mol/m² of an yellow dye-providing compound having the structure shown below, $3 \times 10^{-4}$ mol/m² of an ED compound as shown below, 0.1 g/m² of N,N-diethyllaurylamide, and 0.8 g/m² of gelatin.

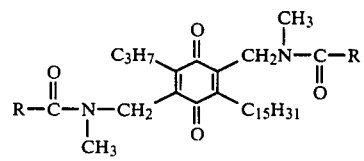

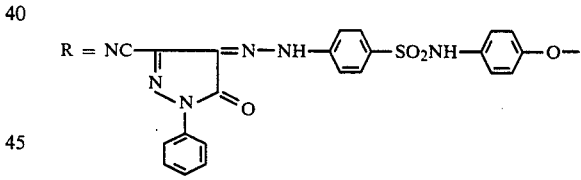

(11) Layer containing 1.0 g/m² (calculated as silver of a blue-sensitive surface latent image-type silver iodobromide emulsion, 0.005 mol/mol Ag of a compound as shown in Table 1, 0.01 g/m² of N,N-diethyllaurylamide, and 0.8 g/m² of gelatin.

(12) Protective layer containing 0.10 g/m² of a polymethyl methacrylate latex (average particle size: 4μ), 1.0 g/m² of gelatin, and 0.02 g/m² of triacroyltriazine as a hardening agent.

Preparation of Cover Sheet

On a transparent polyethylene terephthalate support were coated the following layers (1') to (3') in this order to prepare a cover sheet.

(1') Layer containing 22 g/m² of a copolymer of acrylic acid and butyl acrylate (80:20 by weight) and 0.44 g/m² of 1,4-bis(2,3-epoxypropoxy)-butane.

(2') Layer containing 3.8 g/m² of acetyl cellulose (forming 29.4 g of acetyl groups upon hydrolysis of 100 g of the acetyl cellulose), 0.23 g/m² of a methanol ring-opened product of a copolymer of styrene and maleic anhydride (60:40 by weight) (molecular weight: about 50,000), and 0.154 g/m² of 5-(2-cyano-1-methylethylthio)-1-phenyltetrazole.

(3') Layer 2μ in thickness as prepared by coating a mixture of (a) a styrene/n-butyl acrylate/acrylic acid/N-methylolacrylamide (49.7:42.3:3:5 by weight) copolymer latex and (b) a methyl methacrylate/acrylic acid/N-methylolacrylamide (93:4:3 by weight) copolymer latex (solid content of (a):solid content of (b)=6:4).

Composition of Processing Solution 1-p-Tolyl-4-hydroxymethyl-4-methyl-3-pyrazolidone: 10 g
Methyl hydroquinone: 0.3 g
5-Methylbenzotriazole: 3.5 g
Sodium sulfite (anhydrous): 0.2 g
Carboxymethyl cellulose sodium salt: 58 g
Potassium hydroxide (28% aqueous solution): 200 ml -continued

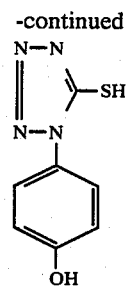

Compound D (for comparison)

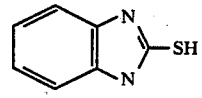

TABLE 1

| Light-Sensitive Sheet No. | Compound | $D_{max}$ | | | $\gamma$*(graduation) | | | $S_{-0.2}$** (Shadow Sensitivity) | | | Remarks |
|---|---|---|---|---|---|---|---|---|---|---|---|
| | | B | G | R | B | G | R | B | G | R | |
| 1 | none (control) | 1.20 | 1.33 | 1.25 | 1.9 | 2.0 | 2.1 | 0 | 0 | 0 | Comparative example |
| 2 | Compound B | 1.80 | 2.25 | 2.35 | 0.4 | 0.45 | 0.5 | −0.5 | −0.75 | −1.0 | Comparative example |
| 3 | Compound C | 1.70 | 2.13 | 2.21 | 0.8 | 0.8 | 0.9 | −0.43 | −0.45 | −0.5 | Comparative example |
| 4 | Compound D | 1.77 | 2.18 | 2.22 | 0.9 | 1.0 | 1.0 | −0.5 | −0.7 | −0.6 | Comparative example |
| 5 | Compound 1 | 1.78 | 2.22 | 2.28 | 2.1 | 2.0 | 2.1 | 0 | 0 | −0.05 | Invention |
| 6 | Compound 5 | 1.72 | 2.18 | 2.19 | 1.9 | 2.1 | 2.2 | −0.05 | −0.05 | −0.05 | " |
| 7 | Compound 9 | 1.80 | 2.20 | 2.33 | 2.1 | 2.3 | 2.5 | 0 | 0 | 0 | " |
| 8 | Compound 16 | 1.65 | 2.05 | 2.09 | 1.8 | 2.0 | 2.0 | −0.1 | −0.1 | −0.1 | " |

Note:
*$\gamma$: Gradients at ($D_{max}$ − 0.2) and ($D_{min}$ + 0.2)
**$S_{-0.2}$: Relative log E at $D_{max}$ − 0.2 (with No. 1 as 0)

Benzyl alcohol: 1.5 ml
Carbon black: 150 g
KBr: 10 g
Water: 685 ml

ED Compound A

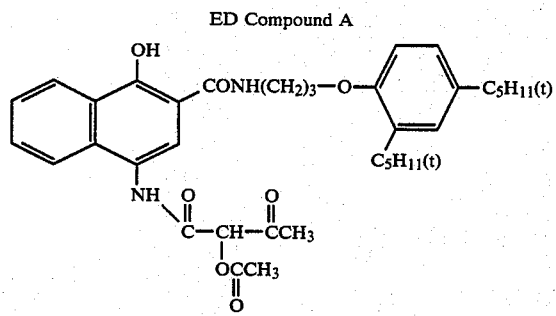

Compound B (for comparison)

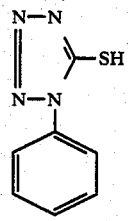

Compound C (for comparison) (Compound (I) disclosed in Japanese Patent Application (OPI) No. 168249/82)

It can be seen from Table 1 that in the light-sensitive sheets (Nos. 2 to 4) of the prior art, although the fogged silver-preventing effect (Dmax up) is observed, the problems of a serious reduction in sensitivity (as determined based on the shadow sensitivity) and a serious recduction in rate of development (low contrast, i.e., decreases) arise, whereas in the light-sensitive sheets of the present invention the fogged silver can be prevented efficiently without causing a substantial reduction in sensitivity and a decrease in rate of development (no decrease in contrast).

EXAMPLE 2

In order to confirm the effect of the present invention, the following light-sensitive and image-receiving sheets were produced.

Light-Sensitive Sheets (Nos. 9 to 15)

On a transparent polyethylene terephthalate support were coated the following layers to produce a light-sensitive sheet.

At the back side:
(a) Light-shielding layer containing 4.0 g/m² of carbon black and 2.0 g/m² of gelatin.

At the emulsion layer side:
(1) Layer containing 2×10⁻⁴ mol/m² of a cyan dye-providing compound as shown below, 2×10⁻⁴ mol/m² of ED Compound A used in Example 1, 0.1 g/m² of N,N-diethyllaurylamide, and 1 g/m² of gelatin.

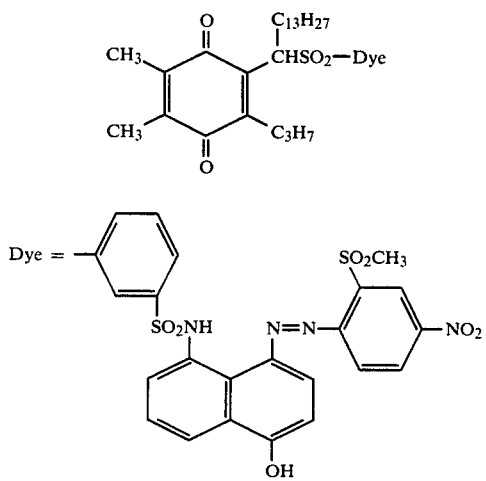

(2) Emulsion layer containing 1 g/m² (calculated as silver) of a red-sensitive surface latent image-type silver chloroiodobromide emulsion (Cl:Br:I-20:75:5), a compound as shown in Table 2 in the amount also as shown in Table 2, and 1 g/m² of gelatin.

(3) Layer containing 1 g/m² of 2,5-di-tert-pentadecyl hydroquinone, and 0.5 g/m² of gelatin.

(4) Layer containing 0.2 g/m² of gelatin.

Image-Receiving Sheet

Paper support: Prepared by coating a 30μ thich polyethylene layer on both sides of a 150μ thick paper; in the polyethylene layer at the image receiving layer side, titanium oxide was dispersed in an amount of 10% based on the weight of the polyethylene.

At the back side:

(a) Light-shielding layer containing 4.0 g/m² of carbon black and 2.0 g/m² of gelatin.

(b) White layer containing 8.0 g/m² of titanium oxide and 1.0 g/m² of gelatin.

(c) Protective layer containing 0.6 g/m² of gelatin.

At the image-receiving layer side:

(1) Neutralizing layer containing 22 g/m² of an acrylic acid/butyl acrylate (8:2 by mol) copolymer (average molecular weight: 50,000).

(2) Neutralization timing layer containing 4.5 g/m² of a 95:5 by weight mixture of cellulose acetate (degree of oxidation: 51.3%; i.e., the amount of acetic acid released through hydrolysis is 0.513 g per gram of the cellulose acetate) and a styrene/maleic anhydride (1:1 by mol) copolymer (average molecular weight: about 10,000).

(3) Layer containing 1.6 g/m² (as total solids) of a mixture of (a) a polymer latex prepared by emulsion polymerization of styrene/butyl acrylate/acrylic acid/N-methylol-acrylamide (49.7:42.3:4:4 by weight) and (b) a polymer latex prepared by emulsion polymerization of methyl methacrylate/acrylic acid/N-methylolacrylamide (93:3:4 by weight) (solid content of (a):solid content of (b)=6:4).

(4) Image-receiving layer containing 3.0 g/m² and a polymer as shown below and 3.0 g/m² of gelatin, as prepared using as a coating aid a compound having the following formula:

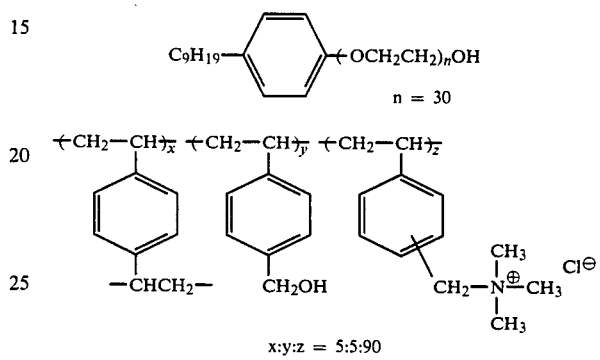

(5) Protective layer containing 0.6 g/m² of gelatin.

Composition of Processing Solution 1-p-Tolyl-4-hydroxymethyl-4-methyl-3-pyrazolidone: 6.9 g
Methylhydroquinone: 0.3 g
5-Methylbenzotriazole: 3.5 g
Sodium sulfite (anhydrous): 0.2 g
Carboxymethyl cellulose sodium salt: 58 g
Potassium hydroxide (28% aqueous solution): 200 ml
Benzyl alcohol: 1.5 ml
Water: 835 ml The above light-sensitive sheet was exposed to light through a color test chart and then superposed on the above image-receiving sheet. Between the light-sensitive and image-receiving sheets, the above processing solution was extended in a thickness of 85μ by means of a press roller.

The processing was conducted at 25° C. In 90 seconds after the processing, the light-sensitive sheet was separated apart from the image-receiving sheet. A reflection density of the image-receiving sheet was measured, and the results are shown in Table 2.

TABLE 2

| Sample No. | Fogged Silver Inhibitor Compound | Amount | Dmax | Dmin | γ* (Gradation Sensitivity) | S₋₀.₂* (Shadow Sensitivity) | Remarks |
|---|---|---|---|---|---|---|---|
| 9 | none (control) | none | 1.05 | 0.28 | 1.1 | 0 | Comparative Example |
| 10 | Compound E | 0.03 mol %/mol Ag | 1.05 | 0.28 | 1.1 | −0.05 | Comparative Example |
| 11 | " | 0.1 mol %/mol Ag | 1.07 | 0.28 | 1.1 | −0.12 | Comparative Example |
| 12 | " | 0.3 mol %/mol Ag | 1.11 | 0.28 | 1.2 | −0.35 | Comparative Example |
| 13 | Compound 9 | 0.01 mol %/mol Ag | 1.45 | 0.28 | 1.4 | 0 | Invention |
| 14 | " | 0.03 mol %/mol Ag | 1.82 | 0.28 | 1.7 | 0 | " |

TABLE 2-continued

| Sample No. | Fogged Silver Inhibitor Compound | Amount | Dmax | Dmin | γ* (Gradation Sensitivity) | S₋₀.₂* (Shadow Sensitivity) | Remarks |
|---|---|---|---|---|---|---|---|
| 15 | " | 0.1 mol %/mol Ag | 2.25 | 0.28 | 1.9 | −0.05 | " |

Note:
*$\gamma$, $S_{-0.2}$: Same as defined in Example 1.

Compound E: 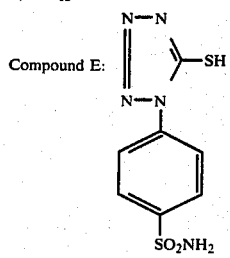

(Compound (IV) as disclosed in Japanese Patent Application (OPI) No. 168249/82)

It can be seen from Table 2 that in the light-sensitive material containing the comparative compound E, if the amount of the compound E is increased, Dmax is increased but the sensitivity seriously drops, whereas in the light-sensitive material of the present invention, even if the additive is added in such amounts that Dmax is sufficiently high, almost no decrease in sensitivity is observed and, furthermore, a reduction in contrast is not observed; rather the contrast is increased. Thus it can be understood that the light-sensitive material of the present invention is a superior photographic light-sensitive material.

While the invention has been described in detail and with reference to specific embodiments thereof, it will be apparent to one skilled in the art that various changes and modifications can be made thereto without departing from the spirit and scope thereof.

What is claimed is:

1. A color diffusion transfer photographic light-sensitive material comprising a support, at least one silver halide layer on the support, said emulsion layer being associated with a dye-providing compound, and an image-receiving layer on the same support as above or on another support, wherein said photographic light-sensitive material is able to provide a transferred dye image composed of a diffusible dye or its precursor released or derived from the dye-providing compound as a result of development under a strong alkaline condition in the presence of at least one meso-ionic 1,2,4-triazolium-3-thiolate compound, said light-sensitive material containing at least one meso-ionic 1,2,4-triazolium-3-thiolate compound.

2. The material as claimed in claim 1, wherein the silver halide emulsion is a surface latent image-type negative emulsion, and the dye-providing compound is of the type that provides a positive transfer dye image.

3. The material as claimed in claim 2, wherein the dye-providing compound is a non-diffusible redox compound releasing a diffusible dye or its precursor upon receipt of at least one electron as a result of development under a strong alkaline condition, which is used in combination with a non-diffusible electron-donating compound or is linked to an electron donating group or its precursor.

4. The material as claimed in claim 1, wherein the meso-ionic 1,2,4-triazolium-3-thiolate compound is represented by the following general formula (I)

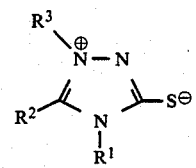

wherein:

$R^1$ is a hydroxyl group, a substituted or unsubstituted alkyl group, a substituted or unsubstituted alkenyl group, a substituted or unsubstituted aryl group, a substituted or unsubstituted heterocyclic group, —$NR^4R^5$ wherein $R^4$ and $R^5$ are each a hydrogen atom, a substituted or unsubstituted alkyl group, a substituted or unsubstituted acyl group, a substituted or unsubstituted aryl group or $R^4$ and $R^5$ may combine together to form a nitrogen-containing hetero ring, a substituted or unsubstituted acyloxy group, or a substituted or unsubstituted alkoxyl group;

$R^2$ is a hydrogen atom, a substituted or unsubstituted alkyl group, a substituted or unsubstituted aryl group, or a substituted or unsubstituted heterocyclic group;

$R^3$ is a substituted or unsubstituted alkyl group, a substituted or unsubstituted alkenyl group, a substituted or unsubstituted aryl group, or a substituted or unsubstituted heterocyclic group; and $R^1$ and $R^2$, or $R^2$ and $R^3$ may combine together to form a 5- to 7-membered, saturated or unsaturated, carbon ring or hetero ring.

5. The material as claimed in claim 4, wherein the substituted or unsubstituted alkyl group represented by $R^1$, $R^2$, $R^3$, $R^4$ or $R^5$ has each from 1 to about 30 carbon atoms where the alkyl group is straight or branched; the substituted or unsubstituted alkyl group or alkenyl group represented by $R^1$, $R^2$, $R^3$, $R^4$ or $R^5$ has each from 3 to aboout 30 carbon atoms where the alkyl group is cyclic; and the substituted or unsubstituted aryl group or heterocyclic group represented by $R^1$, $R^2$, $R^3$, $R^4$ or $R^5$ has each from 1 to about 30 carbon atoms.

6. The material as claimed in claim 5, wherein the substituted or unsubstituted alkyl or alkenyl group has each not more than 10 carbon atoms and the substituted or unsubstitued aryl or heterocyclic group has each not more than 16 carbon atoms.

7. The material as claimed in claim 4, wherein at least one of $R^1$, $R^2$ and $R^3$ is a substituted or unsubstituted phenyl group and the total carbon atoms of $R^1$, $R^2$ and $R^3$ is not less than 7.

8. The material as claimed in claim 4, wherein the meso-ionic 1,2,4-triazolium-3-thiolate compound is selected from the group consisting of

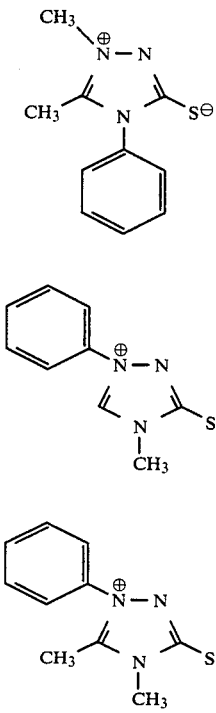

-continued
and

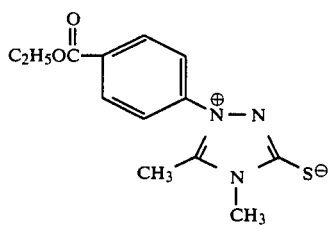

9. The material as claimed in claim 1, wherein the material is a film assembly comprising a support having thereon a light-sensitive element containing at least a light-sensitive silver halide emulsion layer associated with a dye-providing compound and an image-receiving element containing at least an image-receiving layer on the said support or on a different support and a processing element containing at least a strong alkaline solution, at least one of the said light-sensitive element, a cover sheet superposed thereon, the said image-receiving element and the said processing element containing the meso-ionic 1,2,4-triazolium-3-thiolate compound.

10. A color diffusion transfer process of forming a transferred dye image which comprises exposing to light and then developing a photographic light-sensitive material containing a support, at least one silver halide layer on the support, said emulsion layer being associated with a dye-providing compound, and an image-receiving layer on the same support as above or on another support under a strong alkaline condition in the presence of at least one-meso ionic 1,2,4-triazolium-3-thiolate compound, and fixing a transferred dye or precursor thereof released or derived from the dye-providing compound in the image-receiving layer.

* * * * *